United States Patent [19]

Smith et al.

[11] Patent Number: 5,566,221
[45] Date of Patent: Oct. 15, 1996

[54] APPARATUS FOR APPLYING A PREDETERMINED X-RADIATION FLUX TO AN INTERIOR SURFACE OF A BODY CAVITY

[75] Inventors: Donald O. Smith, Lexington; Alan P. Sliski, Lincoln; Kenneth J. Harte, Carlisle; Robert A. Roth, Brookline, all of Mass.

[73] Assignee: Photoelectron Corporation, Lexington, Mass.

[21] Appl. No.: 273,963

[22] Filed: Jul. 12, 1994

(Under 37 CFR 1.47)

[51] Int. Cl.⁶ ........................ A61N 5/10
[52] U.S. Cl. .................... 378/145; 378/65
[58] Field of Search .................. 378/204, 145, 378/64, 65; 128/653.1; 606/130

[56] References Cited

U.S. PATENT DOCUMENTS

| | | |
|---|---|---|
| 2,799,273 | 7/1957 | Oddo . |
| 2,849,002 | 8/1958 | Oddo . |
| 3,752,990 | 8/1973 | Fischer . |
| 4,470,407 | 9/1984 | Hussein ........................ 128/6 |
| 4,608,977 | 9/1986 | Brown . |
| 4,646,338 | 2/1987 | Skillicorn . |
| 4,694,480 | 9/1987 | Skillicorn . |
| 4,932,958 | 6/1990 | Reddy et al. ................ 606/192 |
| 5,002,558 | 3/1991 | Klein et al. ................. 606/192 |
| 5,007,897 | 4/1991 | Kalb et al. .................. 604/43 |
| 5,090,043 | 2/1992 | Parker et al. . |
| 5,153,900 | 10/1992 | Nomikos et al. . |
| 5,165,093 | 11/1992 | Miller et al. . |
| 5,209,725 | 5/1993 | Roth . |

FOREIGN PATENT DOCUMENTS 02-68073  5/1990  Japan .

OTHER PUBLICATIONS

Nseyo et al., *Urology* (1990) vol. XXXVI, No. 5, "Whole Bladder Photodynamic Therapy: Critical Review of Present-Day Technology and Rationale For Development Of Intravesical Laser Catheter and Monitoring System", pp. 398–402.

*Primary Examiner*—Don Wong
*Attorney, Agent, or Firm*—Lappin & Kusmer

[57] ABSTRACT

The present invention is directed to a kit for delivering x-rays to the interior surface of a body cavity. The kit includes an x-ray source and an x-ray source guidance tube. The guidance tube includes an inflatable inelastic balloon disposed about and affixed at its distal end such that when inflated, the central axis of the balloon is coaxial with and is disposed about the central axis of the tubular element. Inflation and deflation of the balloon is controllable from the proximal end of the tubular element. The x-ray source may include an electron activated target for generating x-rays in response to electrons incident on the target. The x-ray source may also includes means for generating an electron beam and steering the beam so that it is incident on the target. The target end is slidably positionable within an interior channel of the source guidance tube.

13 Claims, 2 Drawing Sheets

APPARATUS FOR APPLYING A PREDETERMINED X-RADIATION FLUX TO AN INTERIOR SURFACE OF A BODY CAVITY

BACKGROUND OF DISCLOSURE

The present invention relates to a miniaturized, low power, programmable x-ray source for use in delivering substantially constant or intermittent levels of x-rays to a specified region. More specifically, the invention relates to apparatus and methods for delivering a uniform x-ray flux to an interior surface of a body cavity.

Most conventional medical x-ray sources are large, fixed position machines. Generally, the head of the x-ray tube is placed in one room and the control console in an adjoining area, with a protective wall, equipped with a viewing window, separating the two. The x-ray tube typically is approximately 20 to 35 centimeters (cm) long, and approximately 15 cm in diameter. A high voltage power supply is housed within a container located in a corner of the room containing the x-ray tube. Patients are brought to the machine for diagnostic, therapeutic, or palliative treatment.

Diagnostic x-ray machines are typically operated at with electron acceleration voltages below 150 kilovolts (kV), and at beam currents from approximately 25 to 1200 milliamps (mA). By contrast, the currents in therapeutic units typically do not exceed 20 mA at voltages which may range above 150 kV. When an x-ray machine is operated at nominal voltages of 10 to 140 kV, the emitted x-rays provide limited penetration of tissue, and are thus useful in treating skin lesions. At higher voltages (approximately 250 kV), deep x-ray penetration is achieved, which is useful in the treatment of major body tumors. Super voltage machines, operable in the 4 to 8 megavolt (MV) region, are used to ablate or destroy all types of tumors, except superficial skin lesions.

One disadvantage of most x-ray devices used for therapy is the high voltage, and consequent high energy radiation, required when directed to soft tissue within or beneath bone. One example is in directing x-rays to areas of the human brain, which is surrounded by bone. High energy x-rays are required to penetrate the bone, but often damage the skin and brain tissue between the radiation entry site and the tumor. Another example in radiation therapy is in directing the x-rays to soft tissue located within the body cavity, couched among other soft tissue, or within an internal calciferous structure. Present high-voltage x-ray machines are limited in their ability to selectively provide desired x-ray radiation to such areas.

Another disadvantage of conventional high voltage sources is the damage caused to skin external to the affected organ or tissue. Therefore, prior art high voltage x-ray sources often cause significant damage not only to the target region or tissue, but also to all tissue between the entry site, the target region, and the exit site, particularly when used for human tumor therapy. However, since present devices apply x-ray radiation to target regions internal to a patient from a source external to the target region, such incidental tissue damage is practically unavoidable.

Conventional radiation therapy treatment of the soft tissue that lines body cavities, such as the bladder, vagina and cervix, urethra, uterus, colon, and rectum, involves application of x-radiation from an extra-corporal source. Consequently, such techniques of radiation therapy have the disadvantage that they necessarily radiate areas of the patient between the radiation entry site, the target tissue, and the exit site, causing damage to such tissue.

Conventional methods of radiation treatment for body cavities also have the further disadvantage of failing to provide the ability to establish a uniform dose of radiation to the target tissue. In some cases, it is desirable that radiation treatment of the tissue lining a body cavity provide the same dose of radiation to every segment of the tissue, i.e., a uniform dose. In other cases, specifically contoured non-uniform doses may be desired. The prior art x-ray sources cannot accomplish this for interior body cavities. As used herein, the term "uniform dose" refers to an isodose contour, i.e., a surface over which the flux density is substantially constant.

Some of these disadvantages can be overcome through the use of miniaturized low power x-ray sources, such as the one described in U.S. Pat. No. 5,153,900 issued to Nomikos et al. which is hereby incorporated by reference. These sources can be inserted into, and activated from within, a patient's body. Thus, these sources can generate x-rays local to the target tissue. When such x-ray sources are used to treat the tissue lining a body cavity, the x-rays need not pass through the patient's skin, bone and other tissue prior to reaching the target tissue. However, even utilizing these sources it is difficult to provide a uniform, or other desired, dose of radiation to the target tissue, particularly where the geometry of the target region is not fixed, for example, as in the bladder which has a flexible inner wall without a well-defined shape.

By way of example, some x-ray sources generally of the type disclosed in U.S. Pat. No. 5,153,900 act as point sources of x-ray radiation. Therefore, the strength of the radiation field decreases uniformly in air with approximately the square of the distance from the source (i.e., $1/R^2$). Since body cavities are not generally spherically symmetrical, a point source within a body cavity will not deliver a uniform dose of radiation to the tissue lining the cavity.

It is therefore an object of the invention to provide a method and apparatus for delivering a uniform, or other desired, dose of radiation to the tissue that lines a body cavity.

It is a further object of the invention to provide an apparatus, that includes a miniature low power x-ray source, for delivering a uniform, or other desired, dose of radiation to the tissue that lines a body cavity.

Other objects and advantages of the present invention will become apparent upon consideration of the appended drawings and description thereof.

SUMMARY OF THE INVENTION

In one form, the present invention comprises a method for applying a predetermined x-ray dose to an interior surface of a body cavity. The method includes the steps of providing an x-ray source guidance tube and providing an x-ray source. The guidance tube, intended for insertion into the cavity, includes an elongated first tubular element extending along a central axis. The first tubular element defines an interior channel also extending along the central axis.

An inflatable inelastic balloon is disposed about a first portion of the first tubular element at the end of that element. The balloon extends along a balloon axis from a first end of the balloon to a second end. When fully inflated, the balloon defines a predetermined surface contour about the balloon axis such that the central axis is coincident with the balloon axis. The first portion of the first tubular element extends from the distal end of the tubular element to an intermediate location along that element. The first end of the balloon is affixed to and covers the distal end. The second end of the balloon is affixed to the first tubular element at the intermediate location. An inflation mechanism, at the proximal end of the first tubular element, provides selective control of inflation and deflation of the balloon.

The x-ray source includes a second tubular element having a beam source end and a target end with an electron activated target for generating x-rays in response to electrons incident on the target. The source includes an electron beam generator disposed proximal to the beam source end and a controller for selectively activating the electron beam generator. The source also includes a steering means for steering the beam so that the beam is incident on the target. The second tubular element is slidably positioned within the first interior channel of the guidance tube.

The method includes the steps of inserting the tubular element into the body such that the first portion occupies a predetermined location within the body cavity; operating the inflation mechanism to fully inflate the inelastic balloon thereby establishing a predetermined surface contour which forces the lining of the cavity to conform thereto; inserting the target end into the interior channel of the guidance tube and positioning the target along the balloon axis within the balloon; and operating the controller to generate an electron beam that is incident on the target. Preferably, the step of inflating the balloon may include fully inflating the balloon. In one form, the balloon may be chosen to define a spherical contour disposed about the target at the geometric center of the balloon.

With the invention, a surface of a body cavity is conformed to a predetermined contour and then the x-ray source is adjusted to establish a uniform dose at that surface (i.e., an isodose contour, over which the flux density is substantially constant). The flux density decreases with distance from the source beyond the cavity lining, permitting treatment at the lining surface with diminishing effects in tissue beyond that surface.

In another aspect, the invention provides a kit for applying a predetermined x-ray flux to an interior surface of a body cavity. The kit includes an x-ray source guidance tube and an x-ray source, for example, of the form described above. The target end of the x-ray source is slidably positionable within the interior channel of the tubular element.

Also according to this aspect of the invention, the inelastic balloon may be chosen to define a spherical contour when fully inflated. The balloon may also be chosen so that, when inflated, it has transverse dimensions greater than the largest span of the body cavity.

BRIEF DESCRIPTION OF DRAWINGS

The foregoing and other objects of this invention, the various features thereof, as well as the invention itself, may be more fully understood from the following description, when read together with the accompanying drawings in which.

Like numbered elements in each FIGURE represent the same or similar elements.

DESCRIPTION OF THE PREFERRED EMBODIMENTS

The present invention is a relatively small, electron-beam activated, low power x-ray kit, and a method of use of such kit. The apparatus may be used for medical purposes such as therapeutic radiation of the soft tissue lining body cavities, such as the bladder.

Generally, the apparatus of the present invention includes an electron-beam (e-beam) activated x-ray source which operates at relatively low voltages, i.e. in the range of approximately 10 kV to 90 kV, and relatively small electron beam currents, i.e. in the range of approximately 1 nA to 1 mA, although other ranges may be used as well. At those operating voltages and currents, the x-ray source may be made quite small and be adapted for implantation in medical therapeutic applications. Adequate tissue penetration and dosage may be attained by locating the x-ray source adjacent to or within the region to be irradiated. Thus, the x-rays are emitted from a well-defined, small source located within or adjacent to the region to be irradiated.

Figure 1:
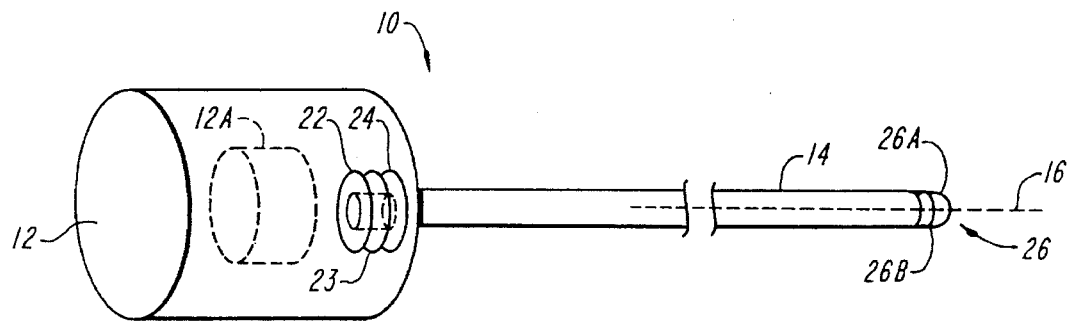
FIG. 1 is a perspective view of a low power x-ray source used in conjunction with the present invention.

FIG. 1 shows one embodiment of an x-ray apparatus 10 forming a part of the present invention. Apparatus 10 includes a housing 12 and an elongated cylindrical probe 14 extending from housing 12 along a reference axis 16 and having a target assembly 26 at its distal end. The housing 12 encloses a high voltage power supply 12A. The probe 14 is a hollow tube having an electron beam generator (cathode) 22 adjacent to the high voltage power supply 12A. Cathode 22 is located in close proximity to an annular focusing electrode 23 typically at nearly the same potential as the cathode 22. An annular anode 24 is positioned approximately 0.5 cm or more from the annular focusing electrode 23. A hollow, tubular probe 14 extends along the same axis as the cathode, grid, and the hole in the anode. Probe 14 is integral with the housing 12 and extends toward a target assembly 26. In various embodiments, parts of the probe 14 may be selectively shielded to control the spatial distribution of x-rays. In addition, the probe 14 may be magnetically shielded to prevent external magnetic fields from deflecting the beam away from the target.

The high voltage power supply establishes an acceleration potential difference between the cathode of generator 22 and the grounded anode 24 so that an electron beam is established along the reference axis 16, through the center hole of the anode and to the target assembly 26, with the region between anode 24 and the target assembly 26 being substantially field free. The beam generation and acceleration components are adapted to establish a thin (e.g. 1 mm or less in diameter) electron beam within the probe 14 along a nominally straight axis 16.

In a preferred embodiment for use in the bladder, the probe 14 is a hollow, evacuated cylinder made of molybdenum (Mo) or mu-metal. The cylinder is 40 cm long, with an interior diameter of 4 mm, and an exterior diameter of 5 mm. For use with other cavities, different geometries are used.

The target assembly 26 includes an emission element consisting of a small beryllium (Be) window 26A coated on the side exposed to the incident electron beam with a thin film or layer 26B of a high-Z element, such as tungsten (W), uranium (U) or gold (Au). By way of example, with electrons accelerated to 30 keV-, a 2.2 micron thick tungsten film absorbs substantially all the incident electrons, while transmitting approximately 95% of any 30 keV-, 88% of any 20 keV-, and 83% of any 10 keV- x-rays generated in that layer. In the preferred embodiment, the beryllium window 26A is 0.5 mm thick with the result that 95% of these x-rays generated in the layer 26B in directions normal to and toward the window, and having passed through the tungsten target layer 26B, are then transmitted through the beryllium window 26A and outward at the distal end of probe 14.

In other forms of the invention, the probe 14 may include at or near its distal tip a capsule containing a radioactive material (such as $I^{125}$) which generates x-rays, rather than including an electron beam generator and x-ray generating target as described above.

The apparatus of FIG. 1 is normally used in a manner where the probe 14 is inserted into a patient while the housing remains outside the patient. In this form, some or all of the various elements shown within housing 12 may alternatively be remotely located.

In one embodiment of the apparatus as shown in FIG. 1, the main body of the probe 14 can be made of a magnetically shielding material such as a mu-metal. Alternatively, the probe 14 can be made of a non-magnetic metal, preferably having relatively high values for Young's modulus and elastic limit. Examples of such material include molybdenum, rhenium or alloys of these materials. The inner or outer surface of probe 14 can then be coated with a high permeability magnetic alloy such as pennalloy (approximately 80% nickel and 20% iron), to provide magnetic shielding. Alternatively, a thin sleeve of mu-metal can be fitted over, or inside of, the probe 14. The x-ray apparatus 10 can then be used in environments in which there are low level dc and ac magnetic fields due to electrical power, the field of the earth, or other magnetized bodies nominally capable of deflecting the electron beam from the probe axis.

In the above-described embodiment, the x-ray emission element of the target assembly 26 is adapted to be adjacent to or within the region of a patient to be irradiated. The proximity of the emission element to the targeted region, e.g. the body cavity, eliminates the need for the high voltages, and consequent high energy radiation of presently used machines, to achieve satisfactory x-ray penetration through the body wall to the body cavity. The low voltage also concentrates the radiation in the targeted tissue, and limits the damage to surrounding tissue and surface skin at the point of entry.

Generally, when treating a body cavity with radiation therapy, it is desirable to uniformly radiate the entire surface of the soft tissue lining the cavity such that an isodose contour is coincident with the surface of the body cavity. An isodose contour is a surface in which the absorbed radiation energy is equal at every point on the surface.

A preferred method of uniformly radiating a body cavity, such as the bladder of a patient, is to use a device to first stretch the cavity into a spherical shape, and then position an omnidirectional x-ray generating probe tip (i.e., a point source) at the center of the cavity. With that configuration, an isodose contour can be established which is coincident with the surface of the body cavity. One device useful for stretching a body cavity to a spherical shape is an inelastic balloon.

Figure 2:
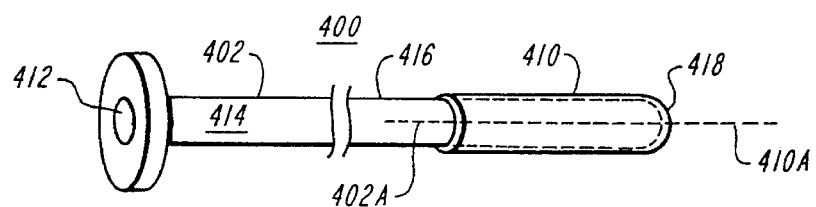
FIG. 2 is a perspective view of an x-ray guidance tube according to the invention in which the balloon is deflated.
Figure 3:
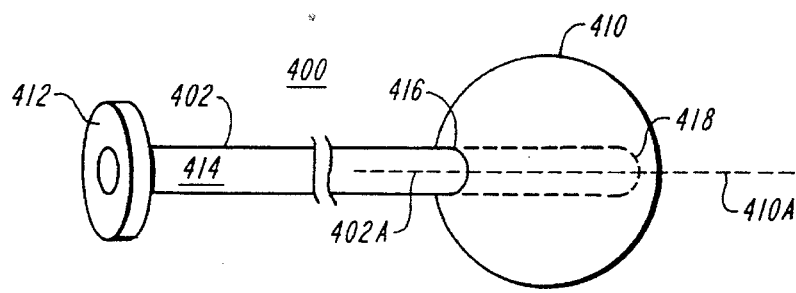
FIG. 3 is a perspective view of the x-ray guidance tube shown in FIG. 2 in which the balloon is inflated.
Figure 4:
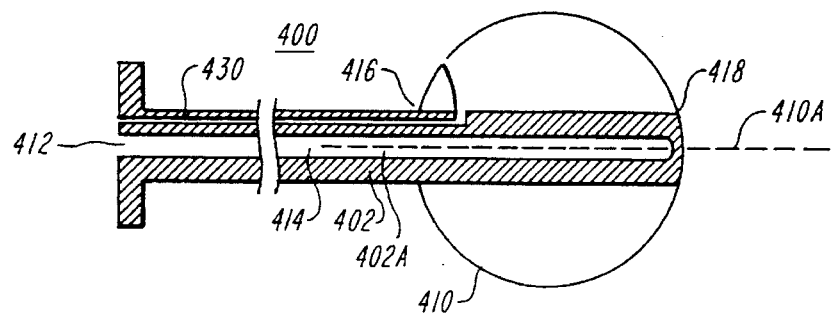
FIG. 4 is a sectional view of the guidance tube of FIG. 3.

FIGS. 2 and 3 show an x-ray source guidance assembly 400 in accordance with the invention for use with the source 10 described above. Those figures show a guidance assembly 400 incorporating a elongated tubular element or catheter 402 having an inflatable inelastic balloon 410 attached to and disposed about its distal end 418. FIG. 4 shows a sectional view of the x-ray source guidance tube 400, with balloon 410 inflated.

Catheter 402 is essentially a hollow tube, open at its proximal end 412 and closed at its distal end 418, and defines a channel 414 which extends through catheter 402 from proximal end 412 to distal end 418 along a balloon axis 410A. Balloon 410 is affixed to tube 402 at an intermediate location 416 (along the catheter 402) and also at distal end 4 18 of catheter 402. The surface of balloon 410 covers, the distal end of catheter 402. For use with the source 10 described above in treating a bladder, the catheter 402 has an outer diameter of 7 mm and an inner diameter slightly in excess of 5 mm. For other cavities, the geometries will differ.

In the illustrated embodiment, the balloon 410 when inflated, defines a spherical interior region. Catheter 402 also includes a second interior channel 430 (shown in the sectional view of FIG. 4) extending from its proximal end 412 to a point near (and within balloon 410) its distal end 418. This channel defines a gas flow path from proximal end 412 to the interior region of balloon 410. Combinations of catheters and inelastic balloons are well known. One such combination is disclosed in U.S. Pat. No. 5,209,725.

Figure 5:
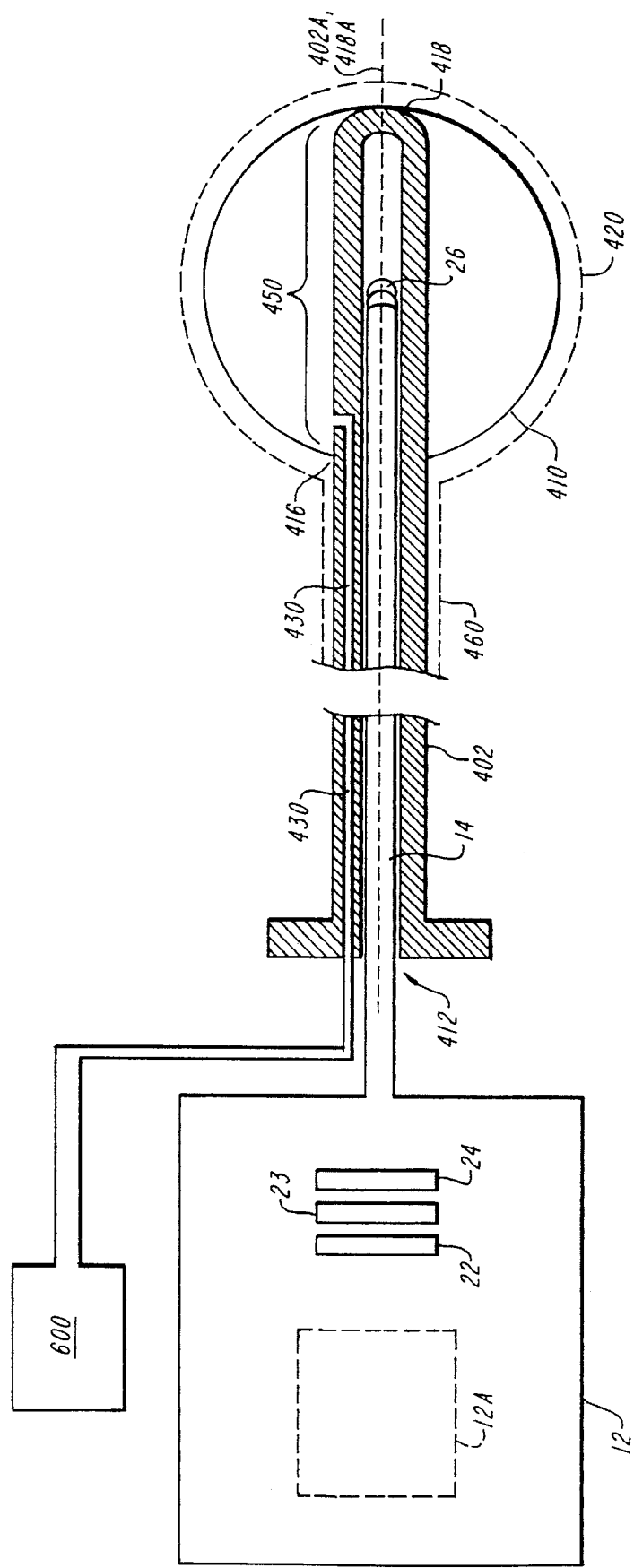
FIG. 5 is a partially sectional view of a kit according to the invention showing the balloon inflated within a patient's bladder and an x-ray probe inserted into the guidance tube.

FIG. 5 shows the guidance assembly 400 positioned such that balloon 410 is inflated within a bladder 420 (shown in dotted lines) of a patient and with probe 14 is inserted within the guidance assembly. An inflation device 600 (for example, an air pump) is coupled to channel 430 in catheter 402, to control inflation and deflation of balloon 410. In practice, the balloon 410 is initially deflated and packed around the exterior of catheter 402 (as shown in FIG. 2). Distal end 418 of catheter 402 is inserted into the urethra 460 of a patient so that the portion 450 of catheter 402 bearing balloon 410 is positioned within the bladder 420. Proximal end 412 remains external to the patient during the entire procedure.

Initially, the inner walls of bladder 420 define a non-uniform shape, but inflation of balloon 410 stretches the walls of bladder 420 into a spherical shape (as shown in FIG. 5). Balloon 410 is preferably an inelastic balloon, selected so that when fully inflated balloon 410 defines a spherical shape slightly larger than the widest span of bladder 420. Further increase in the pressure within balloon 410 will cause balloon 410 to become more rigid, but will not cause further expansion of balloon 410. Selecting balloon 410 so that it has a diameter larger than the widest span of the bladder 420 insures that when balloon 410 is fully inflated vimally the entire surface of the balloon 410 will be in contact with the walls of the bladder 420, and the bladder 420 will be stretched into a spherical shape.

Probe 14 is inserted into catheter 402 such that target assembly 26 is positioned at the center of balloon 410. Probe 14 can be inserted into catheter 402 either prior to or after inflation of balloon 410. Since the exterior of balloon 410 is in contact with the walls of bladder 420, the center of balloon 410 is also the center of bladder 420. Therefore, positioning target assembly 26 at the center of balloon 410, also positions target assembly 26 at the center of bladder 420.

Once target assembly 26 is centered within the bladder, probe 14 is operated, as discussed in connection with FIG. 1, so that x-rays are generated at target 26. Since target 26 is essentially a point source of x-rays, target 26 emits an x-ray field in which the isodose contours are spherical. Centering target assembly 26 within the now spherical bladder 420 insures that the walls of bladder 420 will be coincident with an isodose contour. Thus, uniform radiation is provided to the walls of the bladder 420.

An important feature of the invention is that the structure, as shown in FIG. 5, simplifies centering target assembly 26 within the bladder 420. Affixing balloon 410 to catheter 402 at two locations, 416, 418, insures that a central axis 402A of catheter 402, is coaxial with a central diameter of the balloon 410A and therefore central axis 402A intersects the center of inflated balloon 410, and eliminates any tendency of balloon 410 to wobble. Therefore, target assembly 26 can be reliably positioned at the center of the balloon by positioning the target assembly at the point inside catheter 402 that is midway between location 416 and distal end 418. Selecting balloon 410 to be an inelastic balloon also facilitates the centering process. Inflating balloon to a sufficient pressure to make balloon 410 to be substantially rigid, and to a sufficient diameter to stretch the bladder into a corresponding spherical shape, insures that the center of bladder 420 will be coincident with the center of balloon 410.

In the illustrated embodiment, balloon 410 covers the distal end of catheter 400 to prevent any body fluids from flowing through catheter 402 during the procedure.

After irradiating the bladder, the x-ray source (probe) 14 is withdrawn from the source guidance tube 400 and then balloon 410 is deflated and balloon 410 and catheter 402 are withdrawn from the patient.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A kit for applying x-rays to an interior surface of a body cavity, said kit comprising:
   A. an x-ray source guidance assembly, said assembly including:
   i. a source guidance tube extending along a central axis and having a proximal end and a distal end, said tubular element defining an interior channel extending along said central axis,
   ii. an inflatable inelastic balloon disposed about and extending along a portion of said source guidance tube from an intermediate point on said source guidance tube to said distal end, said balloon being affixed to said source guidance tube at said intermediate point and at said distal end, said balloon defining an interior region disposed about said portion and when said balloon is substantially fully inflated, having a predetermined surface contour and,
   B. an x-ray source cooperative with said x-ray source assembly tube, said x-ray source including an x-ray generator disposed of at or near a first end of an elongated tubular element wherein said first end of said tubular element is slidably positionable within said interior channel of said source guidance tube.

2. A kit for applying x-rays to an interior surface of a body cavity according to claim 1, wherein said x-ray generator is a capsule containing a radioactive material.

3. A kit for applying x-rays to an interior surface of a body cavity according to claim 1, wherein said x-ray generator includes:
   i. said tubular element, said tubular element having a beam source end and a target end and defining an interior region extending along a source axis between said source end and said target end, said target end being said first end,
   ii. beam source means, disposed proximal to said beam source end, for generating an electron beam passing substantially along said source axis toward said target end,
   iii. target means, disposed proximal to said target end, for generating x-rays in response to incidence thereon of said electron beam, and
   iv. control means for selectively activating said beam source means such that said electron beam is incident on said target means.

4. A kit for applying x-rays to an interior surface of a body cavity according to claim 2, wherein said balloon defines a spherical contour when fully inflated.

5. A kit for applying x-rays to an interior surface of a body cavity according to claim 2, wherein said inflated balloon has a diameter greater than a largest span of the body cavity.

6. A kit for applying x-rays to an interior surface of a body cavity according to claim 3, wherein said balloon defines a spherical contour when fully inflated.

7. A kit for applying x-rays to an interior surface of a body cavity according to claim 3, wherein said inflated balloon has a diameter greater than a largest span of the body cavity.

8. A kit for applying x-rays to an interior surface of a body cavity according to claim 3, wherein said source guidance tube further includes a second interior channel extending from said proximal end to a point near said distal end, wherein said second interior channel is in communication to said interior region of said balloon.

9. A method for applying x-rays to an interior surface of a body cavity comprising the steps of:
   A. providing an x-ray source guidance assembly, said assembly including:
   i. a source guidance tube extending along a central axis and having a proximal end and a distal end, said first tubular element defining an interior channel extending along said central axis,
   ii. an inflatable substantially inelastic balloon disposed about and extending along a portion of said source guidance tube from an intermediate point on said source guidance tube to said distal end, said balloon being affixed to said source guidance tube at said intermediate point and said distal end, said balloon defining an interior region disposed about said portion and, when said balloon is substantially fully inflated having a predetermined surface contour,
   B. providing an x-ray source, said x-ray source including an x-ray generator at or near a first end of an elongated tubular element,
   C. inserting said source guidance tube into the body such that said portion occupies a predetermined location within said body cavity,
   D. inflating said balloon whereby said balloon is substantially fully inflated, and
   E. inserting said tubular element within said interior channel such that said target end is positioned at a predetermined location along said source axis within said inflated balloon.

10. A method according to claim 9, wherein said x-ray generator is a capsule containing a radioactive material.

11. A method according to claim 9 wherein said x-ray generator includes:

i. said tubular element, said tubular element having a beam source end and a target end, and defining an interior region extending along a source axis between said source end and said target end, said target end being said first end, ii. beam source means, disposed proximal to said beam source end, for generating an electron beam, iii. target means, disposed proximate to said target end, for generating x-rays in response to incidence thereon of said electron beam, and iv. control means for selectively activating said beam source means such that said electron beam is incident on said target means, and wherein said method includes the further step of operating said controller to generate said electron beam and control said electron beam whereby said electron beam is incident on said target means, thereby generating said x-rays.

12. A method for applying x-rays to an interior surface of a body cavity according to claim 11 wherein said inflating step includes a substep of inflating said balloon such that substantially all of said balloon surface contour contacts the interior surface of said body cavity.

13. A method for applying x-rays to an interior surface of a body cavity according to claim 11 wherein said balloon defines a spherical contour when fully inflated.

* * * * *